United States Patent
Samain et al.

(10) Patent No.: US 7,244,420 B1
(45) Date of Patent: Jul. 17, 2007

(54) COSMETIC COMPOSITION BASED ON ORGANIC SILICON COMPOUNDS COMPRISING AT LEAST A FUNCTION WITH A COSMETIC EFFECT

(75) Inventors: Henri Samain, Bièvres (FR); Isabelle Rollat, Boulogne-Billancourt (FR); Valérie Jeanne Rose, Paris (FR); Clément Sanchez, Gif-sur-Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/089,195

(22) PCT Filed: Sep. 27, 1999

(86) PCT No.: PCT/FR99/02291

§ 371 (c)(1),
(2), (4) Date: Jun. 27, 2002

(87) PCT Pub. No.: WO01/22932

PCT Pub. Date: Apr. 5, 2001

(51) Int. Cl.
*A61Q 5/06* (2006.01)

(52) U.S. Cl. ............... 424/70.12; 106/287.11; 556/425; 556/413; 424/70.122

(58) Field of Classification Search ........... 106/287.11; 424/70.12, 70.122; 556/425, 413
See application file for complete search history.

(56) References Cited

U.S. PATENT DOCUMENTS

| | | | | |
|---|---|---|---|---|
| 3,914,416 A | | 10/1975 | Gueyne et al. ............. 424/184 |
| 5,281,240 A | * | 1/1994 | McGee ........................... 8/405 |
| 5,319,049 A | * | 6/1994 | Yoshioka et al. .............. 528/10 |
| 5,750,092 A | | 5/1998 | Meyer et al. .................. 424/59 |
| 5,954,869 A | * | 9/1999 | Elfersy et al. ......... 106/287.16 |
| 6,113,815 A | * | 9/2000 | Elfersy et al. ............... 252/588 |
| 6,172,250 B1 | | 1/2001 | Seguin et al. ................ 556/407 |
| 6,632,805 B1 | * | 10/2003 | Liebeskind et al. ........... 514/63 |
| 6,762,172 B1 | * | 7/2004 | Elfersy et al. ................ 514/63 |

FOREIGN PATENT DOCUMENTS

| | | |
|---|---|---|
| CH | 535 579 | 4/1973 |
| EP | 0 242 855 | 10/1987 |
| EP | 0 279 623 | 8/1988 |
| EP | 0 464 835 | 1/1992 |
| EP | 0 655 453 | 5/1995 |
| EP | 0 877 027 | 11/1998 |
| FR | 2 746 008 | 9/1997 |
| JP | 63-307811 | 12/1988 |
| WO | 79/00454 | 7/1979 |
| WO | 89/04163 | 5/1989 |

\* cited by examiner

*Primary Examiner*—Margaret G. Moore
(74) *Attorney, Agent, or Firm*—Steptoe & Johnson LLP

(57) ABSTRACT

The invention concerns a composition comprising, in a cosmetically acceptable medium, at least 0.02 weight percent relative to the composition total weight, one or several water soluble organosilicon compounds, selected among silanes having one silicon atom and siloxanes having two or three silicon atoms, the organosilicon compounds comprising two hydroxyl groups or groups capable of being hydrolyzed and two groups not capable of being hydrolyzed per molecule, at least one of the groups not capable of being hydrolyzed being a group with a cosmetic effect and at least one of the remaining functional groups being a group with a solubilizing function. The invention is applicable to hair care compositions.

11 Claims, No Drawings

COSMETIC COMPOSITION BASED ON ORGANIC SILICON COMPOUNDS COMPRISING AT LEAST A FUNCTION WITH A COSMETIC EFFECT

The present invention relates generally to aqueous cosmetic compositions, in particular for treating the hair, comprising unpolymerized or relatively unpolymerized, water-soluble organosilicon compounds containing two nonhydrolyzable functions, at least one of which has a cosmetic effect and at least one other of which has a solubilizing effect, and two hydrolyzable or hydroxy functions per molecule.

It is common practice to attempt to treat the hair so as to improve its properties (disentangling, color or softness). The various treatments developed make it possible to obtain good performance qualities, but, in general, the benefit obtained is not found when the hair is subjected to a washing treatment.

In the case of dyeing, numerous studies have made it possible to develop treatments that give performance qualities, in this instance dying qualities, that are relatively wash-fast ("oxidation" dyeing). However, users remain disappointed with the wash-fastness of their products. Furthermore, the fastness performance qualities achieved to date have been obtained at the expense of the integrity of the hair, since the use of aqueous hydrogen peroxide solution and aqueous ammonia, required for oxidation dyeing, degrades the fiber to a certain extent.

Other systems have been developed, especially using dyes bearing chemical functions having great chemical affinity for the functions of the hair. A large gain in retention is achieved. However, it remains insufficient for many users. Furthermore, since the chemical functions of the hair are highly dependent on the hair's care history, this type of system shows very variable coloring effects depending on the hair onto which these systems are applied.

In the case of hair conditioning treatments, intended to give suppleness to hair that is considered too stiff or to soften hair that is too dry, the current treatments give very poor retention results.

There is thus a need for stable cosmetic compositions, in particular for hair treatments, which make it possible to obtain a sufficient cosmetic effect, in particular for hair in rinse-out or leave-in mode.

The inventors have noted, surprisingly, that it is possible to formulate effective, rinse-fast cosmetic compositions by incorporating into these compositions unpolymerized or relatively unpolymerized organosilicon compounds chosen from organosilanes comprising one silicon atom and organosiloxanes comprising two or three silicon atoms, the organosilicon compounds also comprising per molecule at least two hydroxyl groups or two hydrolyzable functional groups and at least two nonhydrolyzable functional groups, at least one of these nonhydrolyzable functional groups being a functional group having a cosmetic effect, and at least one other of these nonhydrolyzable functional groups being a solubilizing functional group.

The organosilicon compounds according to the invention are capable of forming, in aqueous medium, a nonhybrid compound after self-condensation and evaporation of the support. The expression "nonhybrid compound" means a compound that is chemically homogeneous as regards silicon, that is to say that it contains no other additional metallic or organometallic species.

The compositions according to the invention generally make it possible to obtain shampoo-fast conditioning effects on the hair. In addition, the presence of the nonhydrolyzable functional group, having a cosmetic effect, makes it possible to obtain other cosmetically advantageous retention effects.

In the present invention, the expression "nonhydrolyzable functional group having a cosmetic effect" means any functional chemical group that, after applying the composition to the hair, gives the hair a specific retentive cosmetic effect. Among the specific cosmetic effects that may be mentioned are coloring effects, UV-stabilizing, antibacterial or antifungal effects, and reducing effects.

Thus, for example, when the nonhydrolyzable functional group(s) with a cosmetic effect is (are) group(s) with a coloring effect, the compositions that may be obtained give highly retentive coloring effects, without using active agents that degrade the fiber (aqueous hydrogen peroxide solution or aqueous ammonia) and moreover without being confronted with problems of irregular results when the composition has been applied to hair that is not uniformly sensitized.

Among the nonhydrolyzable functional groups with a coloring effect that may be mentioned are nitroaromatic groups, anthraquinone groups, naphthoquinone groups, benzoquinone groups, azo groups, xanthene groups, triarylmethane groups, azine groups, indoaniline groups, indophenol groups and indoamine groups.

Among the nonhydrolyzable functional groups with a reducing effect, mention may be made of groups comprising a thiol function, a sulfinic acid function or a sulfinic acid salt.

Among the nonhydrolyzable functional groups with an antibacterial function, mention may be made of bisguanidine groups, cationic groups, macrolide groups and phenolic groups.

Among the nonhydrolyzable functional groups with an antifungal effect, mention may be made of pyridine groups, undecylenic groups, salicyl groups and imidazole groups.

At least one of the other nonhydrolyzable functional groups is a solubilizing functional group.

The expression "solubilizing functional group" means any functional chemical group that facilitates the dissolution of the silicon compound in the solvent or mixture of solvents of the composition, in particular in water.

Among the solubilizing nonhydrolyzable functional groups that may be mentioned are any group of atoms bearing an amino radical, a carboxylic acid radical or salts thereof, a sulfonic acid radical or salts thereof, a sulfate radical, a quaternary ammonium radical, a polyalcohol radical such as glycol, a polyether radical such as polyalkylene ether, and a phosphate radical.

Among the amino functions that may be mentioned are primary, secondary or tertiary alkylamines, such as methylamino, alkylamino and propylamino.

Among the carboxylic acid functions and salts thereof, mention may be made of saturated monoacid radicals such as acetic acid, propionic acid, butyric acid, isobutyric acid, valeric acid and isovaleric acid, saturated diacide such as oxalic acid, malonic acid, succinic acid, glutaric acid and adipic acid, unsaturated monoacids such as acrylic acid, methacrylic acid, crotonic acid, maleic acid, fumaric acid and citraconic acid, carbocyclic acids such as benzoic acid, phthalic acid, isophthalic acid and terephthalic acid, hydroxy and alkoxy carboxylic acids such as glycolic acid, lactic acid, tartaric acid and salicylic acid, and salts of these acids, in particular the alkali metal salts and more particularly the sodium and potassium salts of these acids.

Among the quaternary ammonium functions that may be mentioned are tetraalkylammoniums and quaternary alkylarylammoniums, the alkyl and/or aryl groups possibly comprising functions such as acid, hydroxyl, amine and halogen functions, and cyclic and heterocyclic quaternary ammoniums.

Among the sulfonic acids and salts thereof, mention may be made of alkylsulfonic acids such as methylsulfonic acid, arylsulfonic acids such as phenylsulfonic acid, alkoxysulfonic acids such as ethoxysulfonic acid, alkylaryl- and arylalkylsulfonic acids, and salts of these acids, in particular the alkali metal salts of these acids and more particularly the sodium and potassium salts of these acids.

Among the alkyl ether residues that may be mentioned are poly(oxyethylenes), poly(oxypropylenes), poly(oxytetramethylenes) and polyglocols such as poly(ethylene glycol) and poly(propylene glycol).

The recommended solubilizing functions are amine and quaternary ammonium functions.

The hydrolyzable functional groups of the silicon compounds according to the invention are preferably alkoxy, aryloxy or halogen groups.

Among the alkoxy groups that may be mentioned are alkyloxy groups such as methoxy, ethoxy, propoxy and butoxy, and arylalkyloxy groups such as the phenylmethyloxy group.

Among the aryloxy groups that may be mentioned are the phenoxy group and alkylaryloxy groups such as tolyloxy, ethylphenyloxy and propylphenyloxy groups.

Among the halogens that may be mentioned are fluorine, chlorine, bromine and iodine, chlorine being the preferred halogen.

The organosilanes that are preferred according to the invention correspond to the formula:

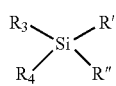

(I)

in which:

R' represents a halogen or an $OR_1$ group and R" represents a halogen or an $OR_2$ group;

$R_1$ and $R_2$ represent, independently of each other, hydrogen or a saturated or unsaturated, linear or branched hydrocarbon-based group optionally bearing additional chemical groups;

$R_3$ is a nonhydrolyzable functional group with a cosmetic effect, and $R_4$ is a nonhydrolyzable functional group with a solubilizing function.

Preferably, $R_1$ and $R_2$ represent hydrogen, a $C_1$ to $C_{12}$ alkyl group, a $C_6$ to $C_{14}$ aryl group, a ($C_1$ to $C_8$)alkyl($C_6$ to $C_{14}$)aryl group and a ($C_6$ to $C_{14}$)aryl($C_1$ to $C_8$)alkyl group.

Preferably, the group $R_3$ is a nonhydrolyzable group with a coloring, UV-stabilizing, antibacterial or antifungal function, or alternatively with a reducing function.

The nonhydrolyzable group $R_4$ with a solubilizing function is preferably an amine group.

The organosiloxanes that are preferred according to the invention correspond to the formula:

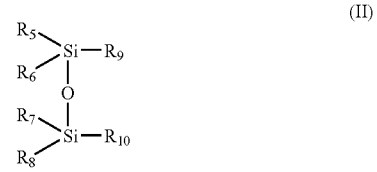

(II)

in which:

$R_5$ represents a nonhydrolyzable functional group with cosmetic activity;

$R_6$ represents a halogen or an $OR'_6$, $R''_6$, $R'''_6$ or $R''''_6$ group;

$R_7$ represents a halogen or an $OR'_7$, $R''_7$, $R'''_7$ or $R''''_7$ group;

$R_8$ represents a halogen or an $OR'_8$, $R''_8$, $R'''_8$ or $R''''_8$ group;

$R_9$ represents a halogen or an $OR'_9$, $R''_9$, $R'''_9$ or $R''''_9$ group; and $R_{10}$ represents a halogen or an $OR'_{10}$, $R''_{10}$, $R'''_{10}$ or $R''''_{10}$ group;

$R'_6$, $R''_6$, $R'_7$, $R''_7$, $R'_8$, $R''_8$, $R'_9$, $R''_9$, $R'_{10}$ and $R''_{10}$ represent, independently of each other, a saturated or unsaturated, linear or branched hydrocarbon-based group optionally bearing additional chemical groups, $R'_6$, $R'_7$, $R'_8$, $R'_9$ and $R'_{10}$ also possibly denoting hydrogen;

$R'''_6$, $R'''_7$, $R'''_8$, $R'''_9$ and $R'''_{10}$ are nonhydrolyzable functional groups with a cosmetic effect;

$R''''_6$, $R''''_7$, $R''''_8$, $R''''_9$ and $R''''_{10}$ are nonhydrolyzable functional groups with a solubilizing function;

at least one of the groups $R_6$ and $R_9$ denotes a halogen or an $OR'_6$ or $OR'_9$ group;

at least one of the groups $R_7$, $R_8$ and $R_{10}$ denotes a halogen or an $OR'_7$, $OR'_8$ or $OR'_{10}$ group; and at least one of the groups $R_6$, $R_7$, $R_8$, $R_9$ and $R_{10}$ denotes an $R''''_6$, $R''''_7$, $R''''_8$, $R''''_9$ and $R''''_{10}$ functional group.

More preferably, the group with a cosmetic function is a group with a coloring, UV-stabilizing, antibacterial or antifungal function or with a reducing function.

The compositions according to the invention contain large concentrations of unpolymerized or relatively unpolymerized silicon compounds, that is to say that they contain at least 0.02% by weight of unpolymerized or relatively unpolymerized silicon compounds relative to the total weight of the composition, and preferably at least 0.5% by weight, which may be up to 50% by weight.

The concentrations of unpolymerized or relatively unpolymerized organosilicon compounds according to the invention are determined by usual methods of analysis such as silicon-29 and proton NMR spectroscopy, and by chromatography.

The compositions according to the invention may be aqueous, aqueous-alcoholic or alcoholic compositions, preferably aqueous compositions.

However, for reasons of use of adjuvants, for example, it may be necessary to add a cosolvent such as ethanol or acetone.

In a known manner, all the compositions of the invention may contain adjuvants commonly used in cosmetics, such as oils, waxes or other common fatty substances; standard gelling agents and/or thickeners; emulsifiers; moisturizers; emollients; sunscreens; hydrophilic or lipophilic active agents, for instance ceramides; free-radical scavengers; surfactants; polymers; proteins; bactericides; sequestering agents; antidandruff agents; antioxidants; preserving agents; fragrances; fillers; dyestuffs.

The amounts of these various adjuvants are those conventionally used in the field under consideration.

Needless to say, a person skilled in the art will take care to select the optional compound(s) added to the composition according to the invention such that the advantageous properties intrinsically associated with the composition in accordance with the invention are not, or are not substantially, adversely affected by the envisaged addition.

The compositions according to the invention may be used in rinse-out or leave-in mode.

The compositions according to the invention may be in any form that is suitable for topical application, especially in the form of solutions of the lotion or serum type; in the form of aqueous gels; in the form of emulsions obtained by dispersing a fatty phase in an aqueous phase (O/W) or, conversely, (W/O), of more or less thick liquid consistency such as more or less unctuous milks and creams.

These compositions are prepared according to the usual methods.

The compositions according to the invention are preferably used as hair products, especially for holding the hairstyle or for shaping the hair. They may also give the hair a temporary coloration or provide the hair with good protection against the effects of UV radiation, or have antibacterial, antifungal and similar actions, depending on the functional group with a cosmetic effect included in the unpolymerized or relatively unpolymerized silicon compounds of the compositions.

The hair compositions according to the invention are preferably styling products such as hairsetting gels or lotions, blow-drying lotions, and fixing and styling compositions such as lacquers or sprays.

The lotions may be packaged in various forms, especially in vaporizers, in pump-dispenser bottles or in aerosol containers to allow an application of the composition in vaporized form or in the form of a mousse. Such packaging forms are indicated, for example, when it is desired to obtain a spray or mousse for fixing or treating the hair.

A subject of the present invention is also the use of the composition according to the invention in a process for treating the hair, in order to hold and/or color it.

According to one embodiment of this process, the composition is applied to rinsed or unrinsed hair, preferably in the form of a spray, either using a pump-dispenser bottle or using an aerosol.

After spraying onto the head of hair, the composition is left to act and to dry.

The hair may be placed in the desired shape, either before the application or immediately after.

The drying time may be variable and depends on the nature of the composition.

EXAMPLE

The composition below according to the invention was prepared:

Aminopropyl-N-(2,4-dinitrophenyl)-2 g aminopropyldiethoxysilane

50/50 aqueous-alcoholic mixture 98 g 10 g of the above composition are applied to a wig of 15 g of prewashed natural hair, containing 70% white hairs.

The composition is left to act for 30 minutes and is then rinsed out with water. The hair is then dried.

After the treatment the hair is dyed. The orange-colored dyeing result obtained is very shampoo-fast. Furthermore, the hair is very shiny and feels like it has a lot of body.

The invention claimed is:

1. A cosmetic composition comprising, in a cosmetically acceptable medium, at least 0.02% by weight, relative to the total weight of the composition, of at least one substantially unpolymerized, water-soluble, organosilicon compound, the organosilicon compound being:

a silane having one silicon atom having the formula:

in which:

R' represents a halogen or an $OR_1$ group;

R" represents a halogen or an $OR_2$ group;

$R_1$ and $R_2$ represent, independently of each other, hydrogen or $C_1$-$C_{12}$ alkyl, $C_6$-$C_{14}$ aryl, ($C_1$-$C_8$ alkyl)($C_6$-$C_{14}$ aryl) or ($C_6$-$C_{14}$ aryl)($C_1$-$C_8$ alkyl) group;

$R_3$ is a nonhydrolyzable functional group with a cosmetic effect that is a coloring, or reducing effect; and $R_4$ is a nonhydrolyzable functional group with a solubilizing function;

or a siloxane having two or three silicon atoms and having at least two hydroxyl or hydrolyzable groups and at least two nonhydrolyzable functional groups per molecule, at least one of the nonhydrolyzable functional groups being a group with a cosmetic effect that is a coloring, UV-stabilizing, antibacterial, antifungal or reducing effect, and at least one of the other nonhydrolyzable functional groups being a group with a solubilizing function.

2. The cosmetic composition of claim 1, wherein the organosilicon compound represents at least 0.5% by weight of the composition.

3. The composition of claim 1, wherein the at least one nonhydrolyzable functional group with a solubilizing function is a primary, secondary or tertiary amine group.

4. The composition of claim 1, wherein the hydrolyzable groups are alkoxy, aryloxy or halogen groups.

5. A cosmetic composition comprising, in a cosmetically acceptable medium, at least 0.02% by weight, relative to the total weight of the composition, of at least one substantially unpolymerized, water-soluble, organosilicon compound, the organosilicon compound being a siloxane having two atoms, the organosilicon compound having at least two hydroxyl or hydrolyzable groups and at least two nonhydrolyzable functional groups per molecule, at least one of the nonhydrolyzable functional groups being a group with a cosmetic effect that is a coloring, UV-stabilizing, antibacterial, antifungal or reducing effect, and at least one of the other nonhydrolyzable functional groups being a group with a solubilizing function, wherein the organosilicon compound has the formula:

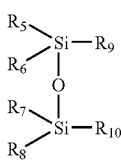

(II)

in which:
- $R_5$ represents a nonhydrolyzable functional group with cosmetic activity that is a coloring, UV-stabilizing, antibacterial, antifungal or reducing effect;
- $R_6$ represents a halogen or an $OR'_6$, $R''_6$, $R'''_6$ or $R''''_6$ group;
- $R_7$ represents a halogen or an $OR'_7$, $R''_7$, $R'''_7$ or $R''''_7$ group;
- $R_8$ represents a halogen or an $OR'_8$, $R''_8$, $R'''_8$ or $R''''_8$ group;
- $R_9$ represents a halogen or an $OR'_9$, $R''_9$, $R'''_9$ or $R''''_9$ group; and
- $R_{10}$ represents a halogen or an $OR'_{10}$, $R''_{10}$, $R'''_{10}$ or $R''''_{10}$ group;
- $R'_6$, $R''_7$, $R'_7$, $R''_7$, $R'_8$, $R''_8$, $R'_9$, $R''_9$, $R'_{10}$ and $R''_{10}$ represent, independently of each other, a substituted or unsubstituted, saturated or unsaturated, linear or branched hydrocarbon-based group;
- $R'_6$, $R'_7$, $R'_8$, $R'_9$ and $R'_{10}$ may represent, independently of each other, hydrogen;
- $R'''_6$, $R'''_7$, $R'''_8$, $R'''_9$ and $R'''_{10}$ are nonhydrolyzable functional groups with a cosmetic effect that is a coloring, UV-stabilizing, antibacterial, antifungal or reducing effect;
- $R''''_6$, $R''''_7$, $R''''_8$, $R''''_9$ and $R''''_{10}$ are nonhydrolyzable functional groups with a solubilizing function;
- at least one of the groups $R_6$ and $R_9$ denotes a halogen or an $OR'_6$ or $OR'_9$ group;
- at least one of the groups $R_7$, $R_8$ and $R_{10}$ denotes a halogen or an $OR'_7$, $OR'_8$ or $OR'_{10}$ group; and
- at least one of the groups $R_6$, $R_7$, $R_8$, $R_9$ and $R_{10}$ denotes an $R''''_6$, $R''''_7$, $R''''_8$, $R''''_9$ and $R''''_{10}$ functional group.

6. The composition of claim 1, wherein the group with a coloring effect is a nitroaromatic group, anthraquinone group, naphthoquinone group, benzoquinone group, azo group, xanthene group, triarylmethane group, azine group, indoaniline group, indophenol group or indoamine group.

7. The composition of claim 5, wherein the group with an antibacterial effect is a bisguanidine group, cationic group, macrolide group or phenolic group.

8. The composition of claim 5, wherein the group with an antifungal effect is a pyridine group, undecylenic group, salicyl group or imidazole group.

9. The composition of claim 1, wherein the composition contains hair product ingredients.

10. The composition of claim 9, wherein the composition contains hair product ingredients for holding the hair or for shaping the hair.

11. A method for treating hair comprising applying to hair an effective amount of a cosmetic composition comprising, in a cosmetically acceptable medium, at least 0.02% by weight, relative to the total weight of the composition, of at least one substantially unpolymerized, water-soluble, organosilicon compound, the organosilicon compound being:
a silane having one silicon atom having the formula:

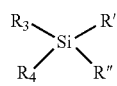

(I)

in which:
- R' represents a halogen or an $OR_1$ group;
- R" represents a halogen or an $OR_2$ group;
- $R_1$ and $R_2$ represent, independently of each other, hydrogen or $C_1$-$C_{12}$ alkyl, $C_6$-$C_{14}$ aryl, ($C_1$-$C_8$ alkyl)($C_6$-$C_{14}$ aryl) or ($C_6$-$C_{14}$ aryl)($C_1$-$C_8$ alkyl) group;
- $R_3$ is a nonhydrolyzable functional group with a cosmetic effect that is a coloring, or reducing effect; and
- $R_4$ is a nonhydrolyzable functional group with a solubilizing function;

or a siloxane having two or three silicon atoms and having at least two hydroxyl or hydrolyzable groups and at least two nonhydrolyzable functional groups per molecule, at least one of the nonhydrolyzable functional groups being a group with a cosmetic effect that is a coloring, UV-stabilizing, antibacterial, antifungal or reducing effect, and at least one of the other nonhydrolyzable functional groups being a group with a solubilizing function.

* * * * *